US00PP23815P2

(12) United States Plant Patent
Hartman

(10) Patent No.: US PP23,815 P2
(45) Date of Patent: Aug. 6, 2013

(54) ***CALADIUM* PLANT NAMED 'WHITE CAP'**

(50) Latin Name: *Caladium×hortulanum*
Varietal Denomination: White Cap

(76) Inventor: Robert Dale Hartman, Lake Placid, FL (US)

( * ) Notice: Subject to any disclaimer, the term of this patent is extended or adjusted under 35 U.S.C. 154(b) by 5 days.

(21) Appl. No.: 13/374,459

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'White Cap', characterized by its upright plant habit; intermediate to tall plant size; uniform plant habit; vigorous and dense growth habit; fancy-type leaves with white-colored venation and white, greyed green and green speckled interveinal areas and dark green-colored margins; and good landscape performance.

4 Drawing Sheets

Botanical designation: *Caladium×hortulanum.*
Cultivar denomination: 'WHITE CAP'.

BACKGROUND OF THE INVENTION

The present invention relates to a new and distinct cultivar of *Caladium* plant, botanically known as *Caladium×hortulanum*, commercially referred to as a fancy leaf-type Caladium and hereinafter referred to by the name 'White Cap'.

The objective of the Inventor's breeding program is to create new Caladium plants that have uniform plant habit, exceptional container and garden performance and attractive foliage coloration.

The new *Caladium* plant originated from a cross-pollination made by the Inventor in April, 2007 in Avon Park, Fla. of *Caladium×hortulanum* 'White Christmas', not patented, as the female, or seed, parent with *Caladium×hortulanum* 'Aaron', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'White Cap'. These characteristics in combination distinguish 'White Cap' as a new and distinct *Caladium* plant:

1. Upright plant habit; intermediate to tall plant size.
2. Uniform plant habit.
3. Vigorous and dense growth habit.
4. Fancy-type leaves with white-colored venation and white, greyed green and green speckled interveinal areas and dark green-colored margins.
5. Good landscape performance.

Plants of the new *Caladium* differ primarily from plants of the female parent, 'White Christmas', in the following characteristics:

1. Plants of the new *Caladium* and 'White Christmas' differ in leaf petiole color.
2. Plants of the new *Caladium* and 'White Christmas' differ in leaf coloration as leaves of plants of 'White Christmas' have dark green-colored venation, white-colored interveinal areas and dark green-colored borders.

Plants of the new *Caladium* differ primarily from plants of the male parent, 'Aaron', in the following characteristics:

1. Plants of the new *Caladium* grew faster than plants of 'Aaron'.
2. Plants of the new *Caladium* and 'Aaron' differ in leaf petiole color.
3. Plants of the new *Caladium* and 'Aaron' differ in leaf coloration as leaves of plants of 'Aaron' have white-colored venation and radiating interveinal areas surrounded with green-colored borders.

Plants of the new *Caladium* can be compared to plants of *Caladium* 'Florida Blizzard', disclosed in U.S. Plant Pat. No. 14,406. In side-by-side comparisons conducted in Avon Park, Fla., plants of the new *Caladium* differed primarily from plants of 'Florida Blizzard' in the following characteristics:

1. Plants of the new *Caladium* and 'Florida Blizzard' differed in leaf petiole color.
2. Plants of the new *Caladium* and 'Florida Blizzard' differed in leaf coloration as leaves of plants of 'Florida Blizzard' had greyed green-colored venation, white-colored interveinal areas with a red purple-colored leaf petiole/leaf junction and dark green-colored borders and margins.

Plants of the new *Caladium* can also be compared to plants of *Caladium* 'Candidum', not patented. In side-by-side comparisons conducted in Avon Park, Fla., plants of the new *Caladium* differed primarily from plants of 'Candidum' in the following characteristics:

1. Plants of the new *Caladium* and 'Candidum' differed in leaf petiole color.
2. Plants of the new *Caladium* and 'Candidum' differed in leaf coloration as leaves of plants of 'Candidum' had green-colored venation, variably white-colored interveinal areas and green-colored and margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'White Cap' grown in a 15-cm container in a shadehouse.

The photograph at the top of the second sheet is a top perspective view of typical plants of 'White Cap' grown in an outdoor nursery.

The photograph at the bottom of the second sheet is a close-up view of typical freshly-harvested tubers and roots of 'White Cap'.

The photograph on the third sheet is a comparison view of potted plants of 'White Cap' grown in 15-cm containers, the plant on the left has had its tuber de-eyed and the plant on the right has not had its tuber de-eyed prior to planting.

The photograph at the top of the fourth sheet is a comparison view of typical potted plants of the male parent, 'Aaron' (left), 'White Cap' (center) and the female parent, 'White Christmas' (right).

The photograph at the bottom of the fourth sheet is a comparison view of typical potted plants of 'Florida Blizzard' (left), 'White Cap' (center) and 'Candidum' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were seven weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification:

*Caladium×hortulanum* 'White Cap'.

Parentage:

*Female, or seed, parent.*—*Caladium×hortulanum* 'White Christmas', not patented.

*Male, or pollen, parent.*—*Caladium×hortulanum* 'Aaron', not patented.

Propagation:

*Type*.—By "chipping" the tubers.

*Time to initiate roots, summer*.—About seven to ten days at 32° C.

*Time to initiate roots, winter*.—About two to three weeks at 24° C.

*Tuber description* (*outdoor nursery-grown plants*).—Appearance: Multi-segmented; individual segments ovate in shape. Height: About 3.2 cm. Diameter: About 5 cm. Texture: Thick and starchy; somewhat brittle. Color: Epidermis, freshly harvested, close to 179C to 179D and 200D; epidermis, dried tuber, close to 200A to 200B; interior, close to 11D; axillary buds, close to N170D. Root description: Thick, fleshy contractile roots; color, close to 155C. Rooting habit: Few lateral branches; moderately dense.

Plant description:

*Plant type*.—Herbaceous perennial; suitable as a potted plant in containers 15-cm to 25-cm and suitable as a landscape plant in shaded areas.

*Plant and growth habit*.—Upright plant habit; intermediate to tall plant size; inverted triangle; vigorous and dense growth habit; rapid growth rate; petioles and leaves arise from one or more growing points on tubers; petioles mostly upright and slightly leaning outwardly with development.

*Plant height, from soil level to top of foliar plane, shadehouse-grown potted plants*.—About 43 cm to 49 cm.

*Plant diameter or spread, shadehouse-grown potted plants*.—About 49 cm to 55 cm.

*Number of clumps per plant, shadehouse-grown potted plants*.—About seven from de-eyed tubers.

*Cataphylls, shadehouse-grown potted plants*.—Length: About 5.5 cm to 8 cm. Width: About 1 cm to 1.2 cm. Shape: Deltoid. Apex: Obtuse to acute. Base: Sheathing the stem. Color, outer surface: Close to 147C moderately streaked and tessellated with close to 147B tinged with close to 200A; with development, color becoming closer to 199A to 199B stained with close to 187A. Color, inner surface: Close to N155C; colors and patterns visible from outer surface.

Foliage description:

*Length, shadehouse-grown potted plants*.—About 20 cm to 25 cm.

*Width, shadehouse-grown potted plants* (*flattened*).—About 13 cm to 17 cm.

*Shape*.—Ovate.

*Apex*.—Acuminate to acute.

*Base*.—Sagittate, peltate.

*Margin*.—Entire; mostly flat with broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Basal notch: Close to 187C. Midrib and primary venation: Close to 191D. Areas surrounding midrib and primary venation: Close to 193D. Secondary venation: Close to 194D. Interveinal areas: Random sectors and spots, close to 194D, close to 155C, close to 155C tinted with close to 146A and close to 147A. Borders and margins: Close to 147A. Developing leaves, lower surface: Basal notch: Close to 187C. Midrib and primary venation: Close to 145B to 145C. Areas surrounding midrib and primary venation: Close to 155C. Interveinal areas: Random sectors and spots, close to 155C, close to 147C and close to 147D overlain with between 147B and 146C. Borders and margins: Close to 191A. Fully expanded leaves, upper surface: Basal notch: Close to 187A. Leaf petiole junction: Close to 191D faintly tinged with close to 181D. Midrib and primary venation: Close to 191D. Areas surrounding midrib and primary venation: Close to 155C tinged with close to 193D. Interveinal areas: Random sectors and spots, close to 194D, close to 155C, close to 146C overlain with close to 146A, and close to 147A tinged with close to 146A. Borders and margins: Close to 147A tinged with close to 146A. Fully expanded leaves, lower surface: Basal notch: Close to 187A. Midrib and primary venation: Close to 145C. Interveinal areas: Random sectors and spots, close to 155C, close to 147C, close to 194A to 194B and close to 194B. Borders and margins: Darker than 191A.

*Petiole*.—Aspect: Mostly erect and leaning outwardly with development; flexible. Length, shadehouse-grown potted plants: About 33 cm to 42 cm. Diameter, distal, shadehouse-grown potted plants: About 3 mm to 4.2 mm. Diameter, proximal, shadehouse-grown potted plants: About 9 mm to 13 mm. Color, shadehouse-grown potted plants: Close to 147B to 147C variably streaked and tessellated with close to 147A tinged with close to 200A; just below the leaf/petiole junction, close to 147D tinged with close to 146D. Wing length, shadehouse-grown potted plants: About 6.4 cm to 8.5 cm. Wing diameter, shadehouse-grown potted plants: About 6 mm to 13 mm. Wing color, shadehouse-grown potted plants, outer surface: Close to 147B moderately streaked and tessellated with close to 147A tinged with close to 200A. Wing color, shadehouse-grown potted plants, inner surface: Close to N155C; outer surface colors and patterns visible.

Inflorescence description: Inflorescence initiation and development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'White Cap' as illustrated and described.

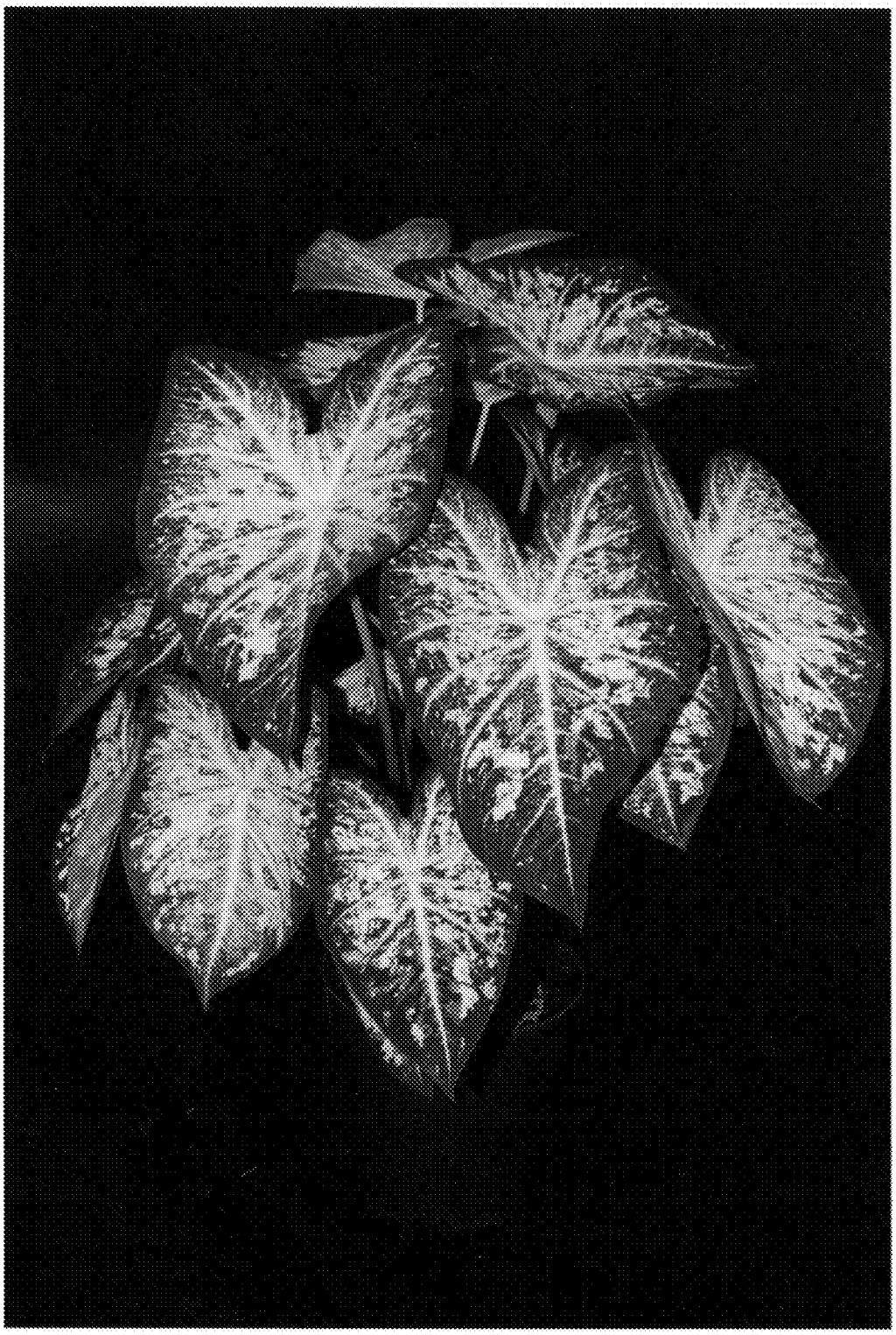

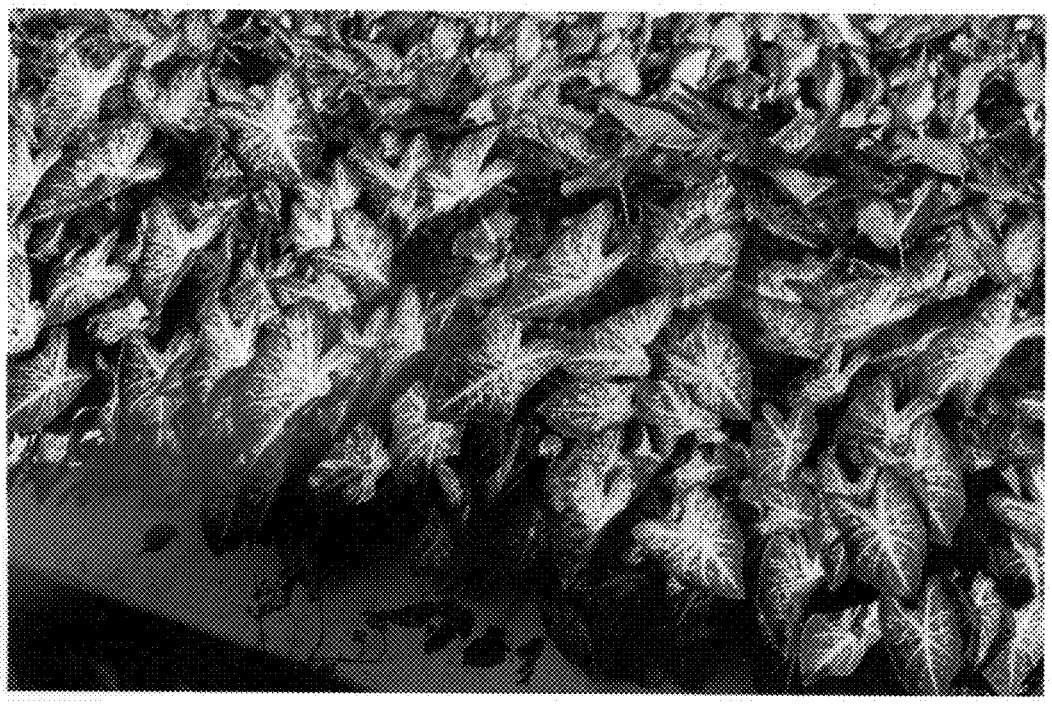
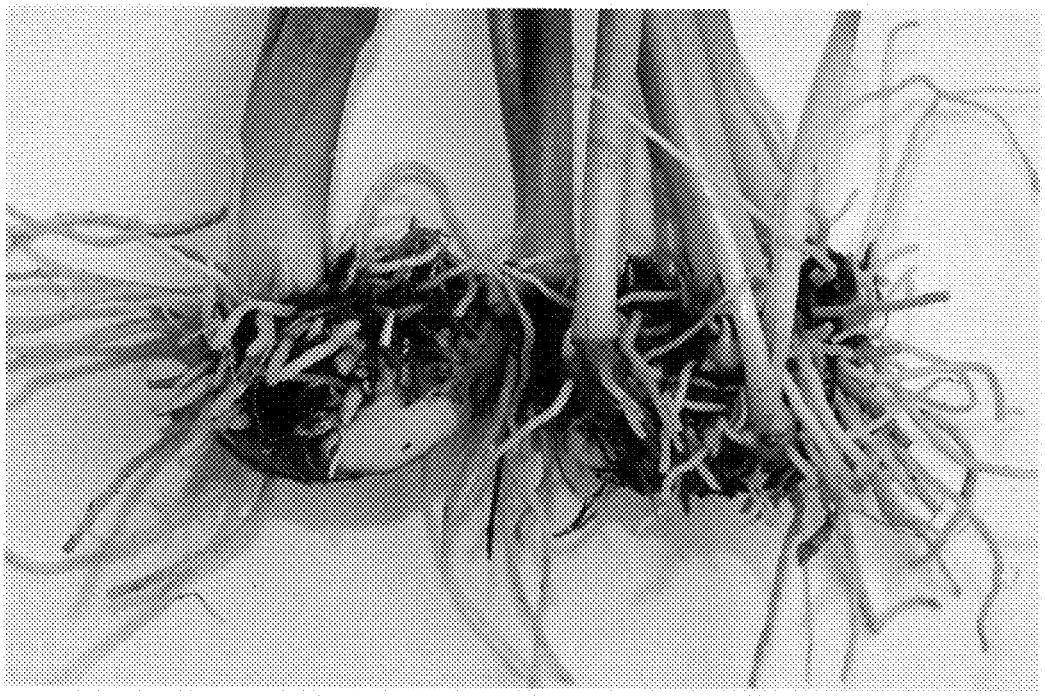

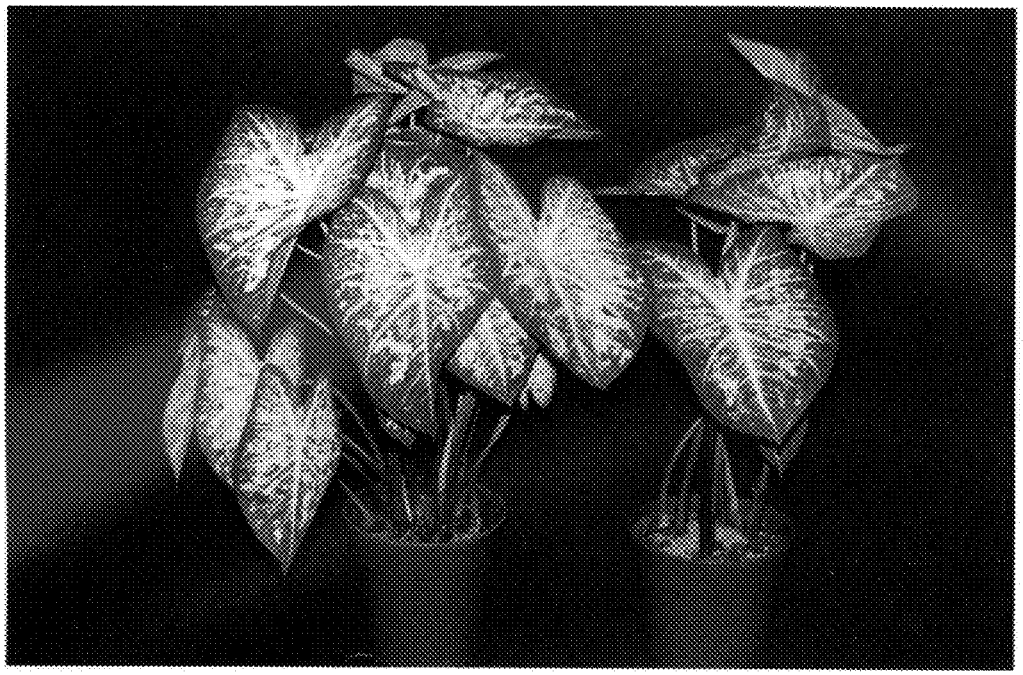

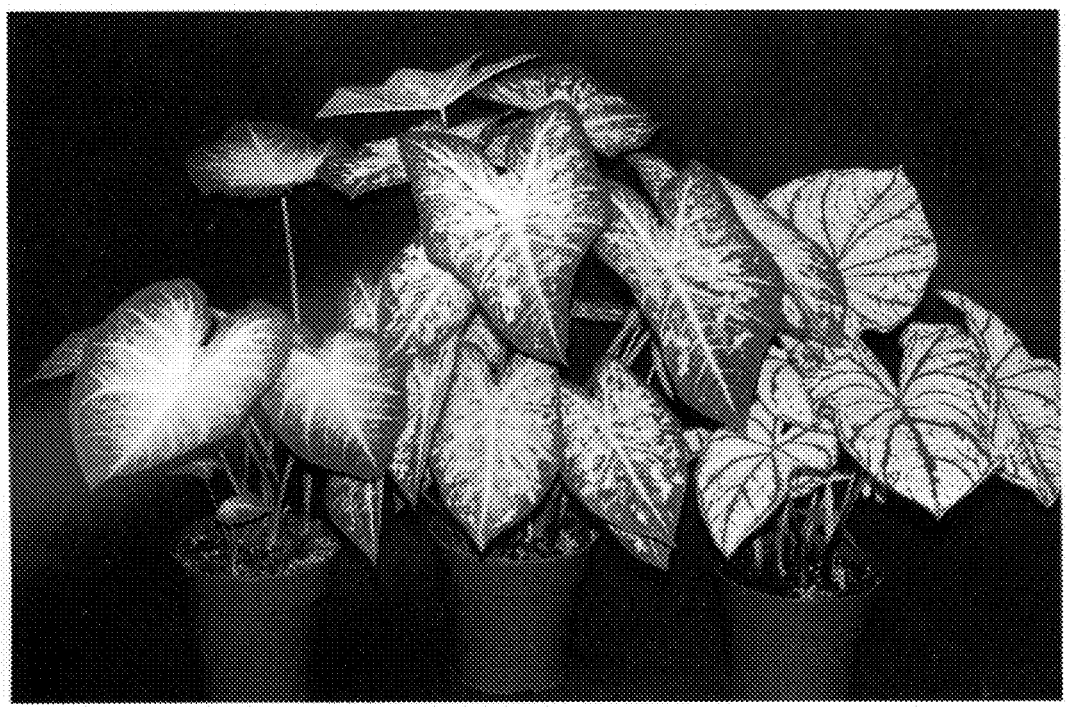
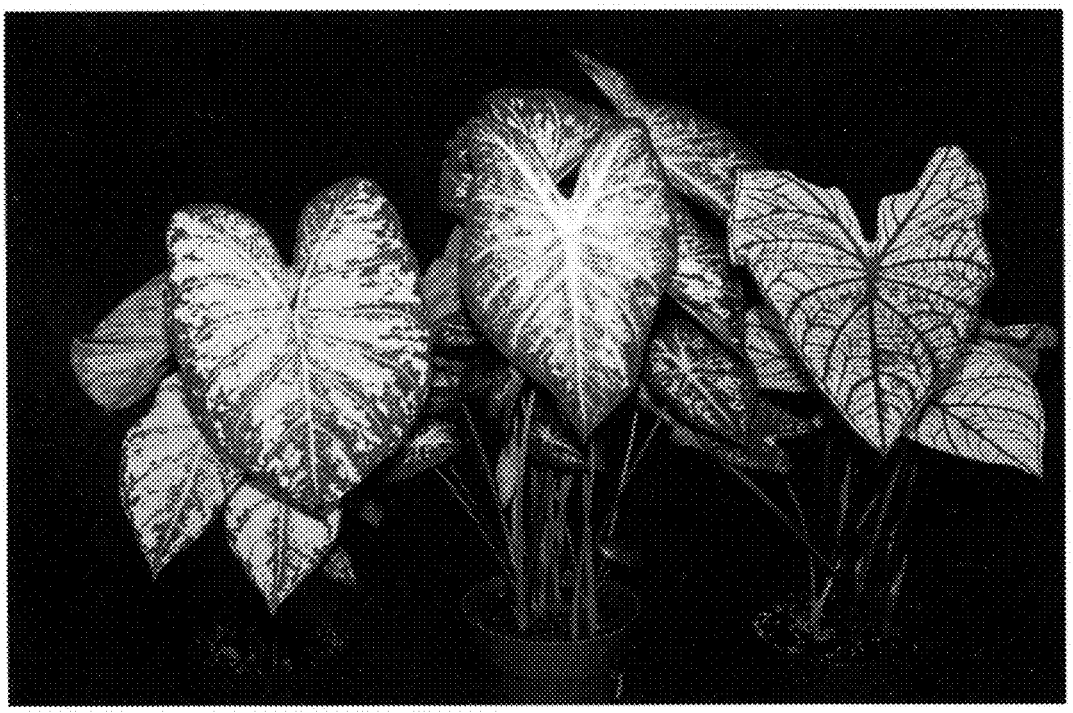

* * * * *